United States Patent [19]
Ohtsubo et al.

[11] Patent Number: 4,889,719
[45] Date of Patent: Dec. 26, 1989

[54] MICROENCAPSULATED ORGANOPHOSPHORUS INSECTICIDAL COMPOSITION FOR AGRICULTURAL USE

[75] Inventors: Toshiro Ohtsubo, Hyogo; Shigenori Tsuda, Kyoto; Yukio Manabe, Osaka; Kiyoshi Kasamatsu; Hisami Takeda, both of Kyogo; Kozo Tsuji, Nara, all of Japan

[73] Assignee: Sumitomo Chemical Company, Ltd., Osaka, Japan

[21] Appl. No.: 215,850

[22] Filed: Jul. 6, 1988

[30] Foreign Application Priority Data

Jul. 6, 1987 [JP] Japan ................... 62-169545

[51] Int. Cl.⁴ ........................................... A01N 25/34
[52] U.S. Cl. .................... 424/408; 424/405; 424/409
[58] Field of Search .................. 424/408; 523/206; 71/88; 514/543, 347

[56] References Cited

U.S. PATENT DOCUMENTS

| | | | |
|---|---|---|---|
| 3,429,827 | 2/1969 | Raas | 252/316 |
| 4,219,570 | 8/1980 | Inazuka et al. | 514/543 |
| 4,285,720 | 8/1981 | Scher | 71/88 |
| 4,460,722 | 7/1984 | Igarashi et al. | 523/206 |
| 4,557,755 | 12/1985 | Takabashi et al. | 71/100 |
| 4,652,574 | 3/1987 | Kato et al. | 514/347 |

FOREIGN PATENT DOCUMENTS

| | | | |
|---|---|---|---|
| 58-144304 | 8/1983 | Japan | 25/28 |
| 1371179 | 10/1974 | United Kingdom . | |
| 2027346 | 8/1979 | United Kingdom . | |

Primary Examiner—Thurman K. Page
Assistant Examiner—P. L. Prater
Attorney, Agent, or Firm—Sughrue, Mion, Zinn, Macpeak & Seas

[57] ABSTRACT

A microencapsulated insecticidal composition has excellent residual effect which comprises an organophosphorus insecticide encapsulated in a wall formed of a polyurea and having an average particle diameter of not more than 80 μm, a wall thickness of not more than 0.3 μm and a ratio of an average particle diameter/wall thickness of not less than 250.

2 Claims, No Drawings

MICROENCAPSULATED ORGANOPHOSPHORUS INSECTICIDAL COMPOSITION FOR AGRICULTURAL USE

BACKGROUND OF THE INVENTION

The present invention relates to a microencapsulated insecticidal composition for agricultural use which comprises an organophosphorus insecticide encapsulated in a wall formed of a polyurea.

Hitherto, an insecticidal composition comprising an organophosphorus insecticide microencapsulated in a wall of polyurethane wall is disclosed in Japanese Patent Kokai (Laid-Open) No. 58 – 144304 and an insecticidal composition comprising parathion microencapsulated in a wall of polyamide-polyurea is disclosed in Japanese Patent Kokai (Laid-Open) No. 48 – 4643, U.S. Ser. No. 149816.

However, no report has been made on insecticidal compositions which comprise an organophosphorus insecticide microencapsulated in a polyurea wall and which have sufficient residual effect.

Under the circumstances, the inventors have made intensive studies on insecticidal activities such as residual effect of insecticidal compositions comprising organophosphorus insecticide for agricultural use microencapsulated in polyurea wall and, as a result, found that average particle diameter, wall thickness and a ratio of an average particle diameter/wall thickness of the microcapsules have a great influence on the insecticidal activities. The present invention has been accomplished on the basis of the above finding.

SUMMARY OF THE INVENTION

That is, the present invention provides a microencapsulated insecticidal composition (hereinafter referred to as "the present composition") enclosed in microcapsules of a polyurea wall which have an average particle diameter of not more than 80 μm, a wall thickness of not more than 0.3 μm and a ratio of an average particle diameter/wall thickness of not less than 250.

Insects to be controlled according to the composition of the invention are pests in paddy fields, vegetable fields, orchards and the like, for example, tobacco cutworm, caterpillars, rice stem borers, aphids, stinkbugs and the like.

The organophosphorus insecticides as active ingredient in the present composition include one or more of those generally used for pest control, preferably those which are of low solubility in water, for example, O,O-dimethyl O-(3-methyl-4-nitrophenyl) phosphorothioate [fenitrothion], O-(4-cyanophenyl) O,O-dimethyl phosphorothioate [cyanophos], 2-methoxy-4H-1,3,2-benzodioxaphosphorine-2-sulfide [salithion], S-[1,2-bis(ethoxycarbonyl)ethyl]O,O-dimethyl phosphorodithioate [malathion], O,O-dimethyl O-(3-methyl-4-methylthiophenyl) phosphorothioate [fenthion], O,O-diethyl O-(2-isopropyl-6-methyl-4-pyrimidinyl) phosphorothioate [diazinon], O-(3,5,6-trichloro-2-pyridyl) O,O-diethyl phosphorothioate [chlorpyrifos], O-(2,4-dichlorophenyl) O-ethyl S-propyl phosphorodithioate [prothiophos]and O-(2,2-dichlorovinyl) O,O-dimethyl phosphate [dichlorvos].

Method of microencapsulation will be explained in detail.

The polyurea wall in the present invention is a polymeric wall having urea bond and basic method for preparation thereof is disclosed, for example, in "Novel Techniques of Microencapsulation and Development of Use and Examples of Application" page 48, Sept. 10, 1978, Keiei Kaihatsu Center.

That is, there are the following two methods: (1) A polyfunctional isocyanate is added to oil phase and a polyfunctional amine is added to aqueous phase, followed by interfacial polymerization; and (2) A polyfunctional isocyanate is added to oil phase, followed by reaction with water to effect interfacial polymerization.

The method (2) is convenient in that polyfunctional amine is not required.

In more detail, for example, a hydrophobic solution containing a polyfunctional isocyanate and an organophosphorus insecticide is dispersed in the form of droplets in an aqueous solution containing a watersoluble polymer as a dispersant. Then, the dispersed solution is heated as it is and is allowed to react with water or a polyfunctional amine having at least two amino groups is added, followed by heating to cause polymerization reaction. After the encapsulation reaction, the resulting capsule suspension as such is diluted with water so as to obtain a desired concentration and, if necessary, a suspension stabilizer is added to obtain a stable slurry type formulation. In case an excess amine is used for polymerization, neutralization, for example, with HCl may be carried out after the reaction.

The polyfunctional amines having at least two NH$_2$ groups include, for example, ethylenediamine, hexamethylenediamine, phenylenediamine, toluenediamine and diethylenetriamine.

The polyfunctional isocyanates include, for example, toluene diisocyanate, hexamethylene diisocyanate, adducts of toluene diisocyanate and trimethylolpropane, self-condensates of hexamethylene diisocyanate, SUMIDUR L ® (made by Sumitomo-Bayer Urethane Co., Ltd.) and SUMIDUR N ® (made by Sumitomo-Bayer Urethane Co., Ltd.).

With reference to composition of the hydrophobic solution, when polyfunctional isocyanate and organophosphorus insecticide are dissolvable with each other, a mixture of them may be directly used. If they have no dissolvability with each other, it is desired to use a uniform mixture of the polyfunctional isocyanate, the organophosphorus insecticide and an organic solvent which is almost immiscible with water and which can dissolve the polyfunctional isocyanate and the organophosphorus insecticide. The organic solvents used for this purpose among ordinary solvents include, for example, hydrocarbons such as xylene, toluene, alkylbenzenes, phenylxylylethane, hexane and heptane, chlorinated hydrocarbons such as chloroform, ketones such as methyl ethyl ketone and cyclohexanone and esters such as diethyl phthalate and n-butyl acetate.

The dispersing agents used for dispersing a hydrophobic solution containing organophosphorus insecticide and polyfunctional isocyanate include, for example, one or more of natural poly saccharides such as gum arabic, semi-synthetic polysaccharides such as carboxymethyl cellulose and methyl cellulose, synthetic polymers such as polyvinyl alcohol and fine mineral powders such as magnesium aluminum silicate. When the dispersibility is weak, this may be improved by adding a known surfactant such as given in H. Horiguchi; "Synthetic Surface Active Agent".

As the suspension stabilizers for capsule slurry, there may be used water-soluble polymers and the like above enumerated as dispersing agents as such, but, if necessary, there may be used one or more of natural polysaccharides such as xanthan gum and locust beam gum, semi-synthetic polysaccharides such as carboxymethyl cellulose, synthetic polymers such as sodium polyacrylate and fine mineral powders such as magnesium aluminum silicate as thickening agents.

Further, if necessary, it is also possible to add a stabilizer such as BHT(2,6-di-t-butyl-4-methylphenol).

The average particle diameter of microcapsules is determined depending mainly on the type and concentration of a dispersing agent used for the dispersion and also on the degree of mechanical agitation during the dispersion. For the measurement of the average particle diameter, the Coulter counter Model TA-II, (available from Nikkaki) may be used, for example.

The wall thickness of microcapsule changes depending on the volume ratio of a core material and a wall material, but can be proximately expressed by the following equation.

$$\text{Thickness} = \frac{Ww}{Wc} \times \frac{\rho c}{\rho w} \times \frac{d}{6}$$

wherein
d: average particle diameter of microcapsules
Wc: weight of a core material
Ww: weight of a wall material
$\rho w$: density of a wall material
$\rho c$: density of a core material The wall thickness in this invention is calculated from the above equation.

The composition of the present invention can be used for control of pests in paddy field, vegetable field ad orchards in such an amount that organophosphorus insecticide which is an active ingredient of the composition of the present invention is normally used for control of the pests. Since the composition has residual effect, it can retain the activity for a long time with application in less amount. Furthermore, as shown in test examples, the composition of the present invention has superior rain fastness.

The present invention is explained in more detail in the following examples, comparative examples and test examples.

EXAMPLE 1

4.4 Gram of "SUMIDUR" L ® (as indicated hereinbefore) was added to 200 g of fenitrothion and stirred until uniform solution was obtained. This solution was added to 350 g of an aqueous solution containing 5% by weight of gum arabic as a dispersing agent and stirring was carried out for several minutes by means of "T.K. autohomomixer" (commercial name, Tokushukika Kogyo K.K.) at room temperature until microdrops were formed. The rate of revolution was 5600 rpm.

Then, the dispersed solution was gently stirred in a constant temperature bath at 60° C. for 24 hours to obtain suspension of microencapsulated products. Water was added to the suspension to make total weight of 1000 g to obtain a slurry of fenitrothion microcapsules of 20% by weight in concentration of an active ingredient (Present composition 1).

The resulting microcapsules had an average particle diameter of 21 μm and a wall thickness of 0.059 μm, and a ratio of an average particle diameter/ wall thickness was 356.

EXAMPLE 2

The procedure of Example 1 was repeated except that amount of "SUMIDUR" L ® (as indicated hereinbefore) was 3.5 g, thereby obtaining a slurry of fenitrothion microcapsules of 20% by weight in concentration of an active ingredient (Present composition 2).

The resulting microcapsules had an average - particle diameter of 21 μm and a wall thickness of 0.047 μm, and a ratio of an average particle diameter/ wall thickness was 447.

EXAMPLE 3

The procedure of Example 1 was repeated except that amount of "SUMIDUR" L ® was 2.5 g, thereby obtaining a slurry of fenitrothion microcapsules of 20% by weight in concentration of an active ingredient (Present composition 3).

The resulting microcapsules had an average particle diameter of 19 μm and a wall thickness of 0.03 μm, and a ratio of an average particle diameter/ wall thickness was 633.

EXAMPLE 4

The procedure of Example 1 was repeated except that amount of "SUMIDUR" L ® was 1.5 g, thereby obtaining a slurry of fenitrothion microcapsules of 20% by weight in concentration of an active ingredient (Present composition 4).

The resulting microcapsules had an average particle diameter of 20 μm and a wall thickness of 0.019 μm, and a ratio of an average particle diameter/ wall thickness was 1053.

EXAMPLE 5

The procedure of Example 1 was repeated except that amount of "SUMIDUR" L ® was 4.4 g and the rate of revolution of T.K. autohomomixer was 7300 rpm, thereby obtaining a slurry of fenitrothion microcapsules of 20% by weight in concentration of an active ingredient.

The resulting microcapsules had an average particle diameter of 10 μm and a wall thickness of 0.028 μm, and a ratio of an average particle diameter/ wall thickness was 357.

EXAMPLE 6

2.5 Gram of "SUMIDUR" L ® (as indicated hereinbefore) was added to 200 g of fenitrothion and stirred until uniform solution was obtained. This solution was added to 400 g of an aqueous solution containing 10% by weight of polyvinyl alcohol as a dispersing agent and stirring was carried out for several minutes by means of "T.K. autohomomixer" (as indicated above) at room temperature until microdrops were formed. The rate of revolution was 6500 rpm.

Then, the dispersed solution was gently stirred in a constant temperature bath at 60° C. for 24 hours to obtain suspension of microencapsulated products. Water was added to the suspension to make total weight of 1000 g to obtain a slurry of fenitrothion microcapsules of 20% by weight in concentration of an active ingredient.

The resulting microcapsules had an average particle diameter of 5 μm and a wall thickness of 0.008 μm, and a ratio of an average particle diameter/ wall thickness was 625.

EXAMPLE 7

The procedure of Example 6 was repeated except that amount of "SUMIDUR" L ® was 2.0 g and 200 g of malathion was used in place of 200 g of fenitrothion, thereby obtaining a slurry of malathion capsules of 20% by weight in concentration of an active ingredient. The resulting microcapsules had an average particle diameter of 5 μm and a wall thickness of 0.006 μm, and a ratio of an average particle diameter/wall thickness was 833.

EXAMPLE 8

The procedure of Example 7 was repeated except that 200 g of cyanophos was used in place of 200 g of malathion, thereby obtaining a slurry of cyanophos microcapsules of 20% by weight in concentration of an active ingredient. The resulting microcapsules had an average particle diameter of 5 μm and a wall thickness of 0.006 μm, and a ratio of an average particle diameter/wall thickness was 833.

EXAMPLE 9

4 Gram of "SUMIDUR" L ® (as indicated hereinbefore) was added to 200 g of fenitrothion and stirred until uniform solution was obtained. This solution was added to 350 g of an aqueous solution containing 5% by weight of gum arabic as a dispersing agent, followed by stirring for several minutes by means of "T.K. autohomomixer" (as indicated above) at room temperature until microdrops were formed. The rate of revolution was 3400 rpm.

Then, the dispersed solution was gently stirred in a constant temperature bath at 70° C. for 20 hours to obtain suspension of microencapsulated products. Thereto was added a solution containing 0.5% by weight of xanthan gum and 1.0% by weight of magnesium aluminum silicate as a thickening agent to make total weight of 1000 g to obtain a slurry of fenitrothion microcapsules of 20% by weight in concentration of an active ingredient.

The resulting microcapsules had an average particle diameter of 45 μm and a wall thickness of 0.115 μm, and a ratio of an average particle diameter/ wall thickness was 391.

EXAMPLE 10

The procedure of Example 9 was repeated except that amount of "SUMIDUR" L ® was 3.5 g, the rate of revolution of T.K. autohomomixer was 5600 rpm and a solution containing 0.8% by weight of xanthan gum as a thickening agent was used in place of the solution containing 0.5% by weight of xanthan gum and 1.0% by weight of magnesium aluminum silicate as a thickening agent, thereby obtaining a slurry of fenitrothion microcapsules of 20% by weight in concentration of an active ingredient.

The resulting microcapsules had an average particle diameter of 20 μm and a wall thickness of 0.045 μm, and a ratio of an average particle diameter/ wall thickness was 444.

EXAMPLE 11

The procedure of Example 6 was repeated except that amount of "SUMIDUR" L ® was 3 g, a mixture of 160 g of fenitrothion and 40 g of malathion was used in place of 200 g of fenitrothion and the rate of revolution of T.K. autohomomixer was 6500 rpm, thereby obtaining a slurry of microcapsules 20% by weight in concentration of active ingredients.

The resulting microcapsules had an average particle diameter of 5 μm and a wall thickness of 0.01 μm, and a ratio of an average particle diameter/ wall thickness was 500.

EXAMPLE 12

3.5 Gram of "SUMIDUR" N ® (as indicated hereinbefore) was added to 200 g of fenitrothion and stirred until uniform solution was obtained. This solution was added to 350 g of an aqueous solution containing 5% by weight of gum arabic as a dispersing agent, followed by stirring for several minutes by means of "T.K. autohomomixer" (as indicated above) at room temperature until microdrops were formed. The rate of revolution was 7300 rpm.

Then, the dispersed solution was gently stirred in a constant temperature bath at 70° C. for 36 hours to carry out reaction, thereby obtaining a suspension of microencapsulated products. Thereto was added water to make total weight of 1000 g and this was diluted two folds with an aqueous solution containing 4% by weight of carboxymethyl cellulose ("CELLOGEN" 3H ®, made by Daiichi Kogyo Seiyaku K.K.), thereby obtaining a slurry of fenitrothion microcapsules of 10% by weight in concentration of an active ingredient.

The resulting microcapsules had an average particle diameter of 10 μm and a wall thickness of 0.022 μm, and a ratio of an average particle diameter/ wall thickness was 455.

EXAMPLE 13

The procedure of Example 1 was repeated except that 3.5 g of "SUMIDUR" L ® AND 0.5 g of toluene diisocyanate ("SUMIDUR" T-80 ®) made by Sumitomo Bayer Urethane Co.) were used in place of "SUMIDUR" L ®, the rate of revolution of T.K. autohomomixer was 5600 rpm and the stirring time in the constant temperature bath was 20 hours, thereby obtaining a slurry of fenitrothion microcapsules of 20% by weight in concentration of an active ingredient.

The resulting microcapsules had an average particle diameter of 19 μm and a wall thickness of 0.051 μm, and a ratio of an average particle diameter/ wall thickness was 373.

EXAMPLE 14

3.5 Gram of "SUMIDUR" L ® (as indicated hereinbefore) was added to 200 g of fenitrothion and stirred until uniform solution was obtained. This solution was added to 350 g of an aqueous solution containing 5% by weight of gum arabic as a dispersing agent, followed by stirring for several minutes by means of "T.K. autohomomixer" (as indicated above) at room temperature until microdrops were formed. The rate of revolution was 5600 rpm. Then, after adding dropwise 5 g of ethylenediamine to the reaction system, the dispersed solution was gently stirred in a constant temperature bath at 50° C. for 30 hours, thereby obtaining a suspension of microencapsulated products. After making the pH of the suspension neutral with 1N HCl, thereto was added water to make total weight of 1000 g, thereby obtaining a slurry of fenitrothion microcapsules of 20% by weight in concentration of an active ingredient.

The resulting microcapsules had an average particle diameter of 19 μm and a wall thickness of 0.051 μm, and a ratio of an average particle diameter/ wall thickness was 373.

EXAMPLE 15

The procedure of Example 1 was repeated except that amount of "SUMIDUR" L ® was 4 g and the rate of revolution of T.K. autohomomixer was 1800 rpm, thereby obtaining a slurry of fenitrothion microcapsules of 20% by weight in concentration of an active ingredient.

The resulting microcapsules had an average particle diameter of 80 μm and a wall thickness of 0.204 μm, and a ratio of an average particle diameter/ wall thickness was 392.

EXAMPLE 16

The procedure of Example 1 was repeated except that amount of "SUMIDUR" L ® was 4 g, a mixture of 180 g of fenitrothion and 20 g of cyclohexyl acetate was used in place of fenitrothion alone and the number of revolution of T.K. autohomomixer was 5600 rpm, thereby obtaining a slurry of fenitrothion microcapsules of 18% by weight in concentration of an active ingredient.

The resulting microcapsules had an average particle diameter of 20 μm and a wall thickness of 0.051 μm, and a ratio of an average particle diameter/ wall thickness was 392.

COMPARATIVE EXAMPLE 1

The procedure of Example 1 was repeated except that amount of "SUMIDUR" L ® was 10 g and the rate of revolution of T.K. autohomomixer was 5600 rpm, thereby obtaining a slurry of fenitrothion microcapsules of 20% by weight in concentration of an active ingredient (Comparative composition 1).

The resulting microcapsules had an average particle diameter of 19 μm and a wall thickness of 0.122 μm, and a ratio of an average particle diameter/ wall thickness was 156.

COMPARATIVE EXAMPLE 2

The procedure of Example 1 was repeated except that amount of "SUMIDUR" L ® was 50 g and the rate of revolution of T.K. autohomomixer was 5600 rpm, thereby obtaining a slurry of fenitrothion microcapsules of 20% by weight in concentration of an active ingredient (Comparative composition 2).

The resulting microcapsules had an average particle diameter of 20 μm and a wall thickness of 0.637 μm, and a ratio of an average particle diameter/ wall thickness was 31.

COMPARATIVE EXAMPLE 3

A fenitrothion emulsifiable concentrate having an active ingredient concentration of 50% by weight was prepared by a usual manner using the following recipe (Comparative Composition 3).

| Fenitrothion | 50 parts by weight |
| --- | --- |
| "SORPOL"1200K (surface active agent made by Toho Kagaku K. K.) | 10 parts by weight |
| Xylene | balance |
| | 100 parts by weight |

TEST EXAMPLE 1

Leaves of cabbages were dipped in each test composition indicated in Table 1 diluted with water to a prescribed concentration for 1 minute. After drying, the thus treated leaves of cabbages were placed in cups of 12 cm in diameter together with 10 tobacco cutworm (third instar larvae). After 48 hours, the mortality was checked and $LC_{50}$ (concentration at which 50% of insects were killed) was obtained. The test was repeated three times.

The results are shown in Table 1.

TABLE 1

| Test composition | $LC_{50}$ (ppm) |
| --- | --- |
| The present composition 1 | 109 |
| The present composition 2 | 103 |
| The present composition 3 | 92 |
| The present composition 4 | 77 |
| Comparative composition 1 | 400 |
| Comparative composition 2 | >400 |
| Comparative composition 3 | 132 |

As shown above, the present compositions were superior to the comparative compositions in the insecticidal efficacy for tobacco cutworm.

TEST EXAMPLE 2

Each test composition as shown in Table 2 which was diluted to a prescribed concentration with water was sprayed by means of a spray gun over potted cabbages mounted on a turn table in an amount of 50 ml per five pots. Each dilution contained 0.02% by weight of Tokusei Rino ® (made by Nippon Noyaku K.K.). The thus treated cabbage pots were allowed to stand in a glass greenhouse and leaves of the cabbages were cut away after a prescribed period of time and were placed in cups having diameter of 12 cm together with 10 tobacco cutworm (third instar larvae). After 48 hours, the mortality was checked. The test was repeated three times. The results are shown in Table 2.

TABLE 2

| Test composition | Concentration (ppm) | Mortality (%) at the indicate days after treatment | | | |
| --- | --- | --- | --- | --- | --- |
| | | 0 | 2 days | 8 days | 14 days |
| The present composition 1 | 500 | 100 | 97 | 37 | 13 |
| 2 | 500 | 100 | 80 | 53 | 33 |
| 3 | 500 | 100 | 87 | 60 | 50 |
| 4 | 500 | 100 | 100 | 63 | 23 |
| Comparative composition 1 | 500 | 70 | 63 | 14 | 0 |
| 3 | 500 | 97 | 60 | 0 | 0 |
| Non-treatment | — | 0 | 0 | 0 | 0 |

As shown above, the present compositions retained their insecticidal efficacy for tobacco cutworms for a long period of time and thus exhibited excellent residual effect.

TEST EXAMPLE 3

Each test composition as shown in Table 3 which was diluted to a concentration of 500 ppm with water was sprayed by means of a spray gun over potted cabbages mounted on a turn table in an amount of 50 ml per five pots. Each dilution contained 0.02% by weight of Tokusei Rino ® (made by Nippon Noyaku K.K.). Just after spraying, the thus treated cabbage pots were subjected to rainfall test of 40 mm (1 hour) by a raining device. After drying, leaves of the cabbages were cut away and were placed in cups having diameter of 12 cm together with 10 tobacco cutworm(third instar larvae). After 48 hours, the mortality was checked. The test was repeated three times. The results are shown in Table 3.

TABLE 3

| Test composition | Mortality (%) | |
|---|---|---|
| | Rainfall | No rainfall |
| The present composition 1 | 37 | 100 |
| The present composition 2 | 48 | 100 |
| The present composition 3 | 67 | 100 |
| The present composition 4 | 73 | 100 |
| Comparative composition 1 | 0 | 73 |
| Comparative composition 3 | 3 | 90 |

As shown above, the present compositions were superior in rain fastness to the comparative compositions.

As explained here, the microencapsulated organophosphorus insecticidal composition of the present invention has an excellent residual effect and hence efficacy of organophosphorus insecticides for agricultural use can be further enhanced. Thus, this is useful.

We claim:

1. A microencapsulated insecticidal composition which comprises an organophosphorus insecticide selected from the group consisting off fenitrothion, cyanophos, salithion, malathion, fenthion, diajinon, chloropyrifos, prothiophos and dichlorvos encapsulated in a wall formed of a polyurea and having an average particle diameter of not more than 80 μm, a wall thickness of not more than 0.3 μm and a ratio of an average particle diameter/wall thickness of not less than 250.

2. The insecticidal composition according to claim 1 wherein the organophosphorus insecticide is fenitrothion.

* * * * *